United States Patent
Rajasekaran

(10) Patent No.: US 7,776,548 B2
(45) Date of Patent: Aug. 17, 2010

(54) ENDOCYTOTIC PATHWAY DELIVERY VEHICLE FOR TARGETING DRUGS AND ANTIBODIES TO PROSTATE AND OTHER TISSUES

(75) Inventor: Ayyappan K. Rajasekaran, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 368 days.

(21) Appl. No.: 11/241,416

(22) Filed: Sep. 30, 2005

(65) Prior Publication Data

US 2006/0069241 A1  Mar. 30, 2006

Related U.S. Application Data

(60) Provisional application No. 60/615,041, filed on Sep. 30, 2004.

(51) Int. Cl.
*G01N 33/53* (2006.01)
*A61K 39/00* (2006.01)
*C07K 14/00* (2006.01)

(52) U.S. Cl. ............... 435/7.1; 424/134.1; 530/350

(58) Field of Classification Search .......... None
See application file for complete search history.

(56) References Cited

OTHER PUBLICATIONS

A Novel Cytoplasmic Tail MXXXL Motif Mediates the Internalization of Prostate-specific Membrane Antigen. Sigrid A. Rajasekaran, Gopalakrishnapillai Anilkumar, Eri Oshima, James U. Bowie, He Liu, Warren Heston, Neil H. Bander, and Ayyappan K. Rajasekaran Mol. Biol. Cell 2003 14: 4835-4845.*
Prostate-specific Membrane Antigen Association with Filamin A Modulates Its Internalization and NAALADase Activity. Gopalakrishnapillai Anilkumar, Sigrid A. Rajasekaran, Song Wang, Oliver Hankinson, Neil H. Bander, and Ayyappan K. Rajasekaran. Cancer Res 2003 63: 2645-2648.*
Rajasekaran, et al. A Novel Cytoplasmic Tail MXXXL Motif Mediates the Internalization of Prostate-specific Membrane Antigen. Mol. Biol. Cell 2003 14: 4835-4845.*

* cited by examiner

*Primary Examiner*—Anand U Desai
*Assistant Examiner*—Kagnew H Gebreyesus
(74) *Attorney, Agent, or Firm*—Berliner & Associates

(57) ABSTRACT

A chimeric transmembrane protein comprising a membrane-spanning polypeptide and an internalization motif of the sequence MXXXL, where X is any amino acid. The chimeric protein can be expressed on the surface of a cell and internalized. Polynucleotides and expression vectors encoding chimeric transmembrane proteins are also provided. Expression of chimeric proteins in the plasma membrane of target cells, followed by binding of antibodies to the chimeric proteins, where the antibodies are conjugated to a cytotoxic agent, provides a means to deliver the cytotoxic agent to the inside of the target cells.

13 Claims, 9 Drawing Sheets

| Construct | Cytoplasmic Tail Sequence | | | | | | | | | | | | | | | | | Int |
|---|---|---|---|---|---|---|---|---|---|---|---|---|---|---|---|---|---|---|
| PSMA | | | | | | | | | | | | | | | | | | |
| Wt | M | W | N | L | L | H | E | T | D | S | A | V | A | T | A | R | R | P | R | + |
| Δcd | M | → | | | | | | | | | | | | | A | R | R | P | R | - |
| Ala 4,5 | - | - | - | A | A | - | - | - | - | - | - | - | - | - | - | - | - | - | - | - |
| Ala 4 | - | - | - | A | - | - | - | - | - | - | - | - | - | - | - | - | - | - | - | + |
| Ala 5 | - | - | - | - | A | - | - | - | - | - | - | - | - | - | - | - | - | - | - | - |
| Ala 2 | - | A | - | - | - | - | - | - | - | - | - | - | - | - | - | - | - | - | - | + |
| Ala 3 | - | - | A | - | - | - | - | - | - | - | - | - | - | - | - | - | - | - | - | + |
| Ala 6 | - | - | - | - | - | A | - | - | - | - | - | - | - | - | - | - | - | - | - | + |
| Ala 7 | - | - | - | - | - | - | A | - | - | - | - | - | - | - | - | - | - | - | - | + |
| Ala 8 | - | - | - | - | - | - | - | A | - | - | - | - | - | - | - | - | - | - | - | + |
| Ala 9 | - | - | - | - | - | - | - | - | A | - | - | - | - | - | - | - | - | - | - | + |
| Ala 10 | - | - | - | - | - | - | - | - | - | A | - | - | - | - | - | - | - | - | - | + |
| Val 14 | - | - | - | - | - | - | - | - | - | - | - | - | - | V | - | - | - | - | - | + |
| Ala 8,10,14 | - | - | - | - | - | - | - | A | - | A | - | - | - | A | - | - | - | - | - | + |
| Δ6-14 | M | W | N | L | L | → | | | | | | | | | A | R | R | P | R | + |
| MA(5) | M | W | N | L | L | H | E | T | D | S | A | V | A | T | A | R | R | P | R | - |
| | A | A | A | A | A | | | | | | | | | | | | | | | |
| | | | | | | | | | | | | | | | | | | | | |
| Tac | | | | | | | | | | | | | | | | | | | | |
| Tac Wt | R | R | Q | R | K | S | R | R | T | I | | | | | | | | | | + |
| Tac-MWNLL | - | - | - | - | - | - | - | - | - | L | L | N | W | M | | | | | | + |
| Tac-MWNAA | - | - | - | - | - | - | - | - | - | A | A | N | W | M | | | | | | - |
| Tac-MWNAL | - | - | - | - | - | - | - | - | - | L | A | N | W | M | | | | | | + |
| Tac-MWNLA | - | - | - | - | - | - | - | - | - | A | L | N | W | M | | | | | | - |
| Tac-AWNAL | - | - | - | - | - | - | - | - | - | L | A | N | W | A | | | | | | - |
| Tac-MAWNAL | - | - | - | - | - | - | - | - | - | L | A | N | W | A | M | | | | | - |

FIG. 1

```
                        SEQUENCE LISTING

<160> NUMBER OF SEQ ID NOS: 31

<210> SEQ ID NO 1
<211> LENGTH: 19
<212> TYPE: PRT
<213> ORGANISM: Human

<400> SEQUENCE: 1

Met Trp Asn Leu Leu His Glu Thr Asp Ser Ala Val Ala Thr Ala Arg
1               5                   10                  15

Arg Pro Arg

<210> SEQ ID NO 2
<211> LENGTH: 6
<212> TYPE: PRT
<213> ORGANISM: Artificial Sequence
<220> FEATURE:
<223> OTHER INFORMATION: deletion mutant
<220> FEATURE:
<221> NAME/KEY: misc_feature
<223> OTHER INFORMATION: deletion mutant

<400> SEQUENCE: 2

Met Ala Arg Arg Pro Arg
1               5

<210> SEQ ID NO 3
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 3

Met Trp Asn Ala Ala His Glu Thr Asp Ser Ala Val Ala Thr Ala Arg
1               5                   10                  15

Arg Pro Arg

<210> SEQ ID NO 4
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 4
```

Met Trp Asn Ala Leu His Glu Thr Asp Ser Ala Val Ala Thr Ala Arg
1               5                   10                  15

Arg Pro Arg

<210> SEQ ID NO 5
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 5

Met Trp Asn Leu Ala His Glu Thr Asp Ser Ala Val Ala Thr Ala Arg
1               5                   10                  15

Arg Pro Arg

<210> SEQ ID NO 6
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 6

Met Ala Asn Leu Leu His Glu Thr Asp Ser Ala Val Ala Thr Ala Arg
1               5                   10                  15

Arg Pro Arg

<210> SEQ ID NO 7
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 7

Met Trp Ala Leu Leu His Glu Thr Asp Ser Ala Val Ala Thr Ala Arg
1               5                   10                  15

Arg Pro Arg

<210> SEQ ID NO 8
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 8

Met Trp Asn Leu Leu Ala Glu Thr Asp Ser Ala Val Ala Thr Ala Arg
1               5                   10                  15

Arg Pro Arg

<210> SEQ ID NO 9

```
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 9

Met Trp Asn Leu Leu His Ala Thr Asp Ser Ala Val Ala Thr Ala Arg
1               5                   10                  15

Arg Pro Arg

<210> SEQ ID NO 10
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 10

Met Trp Asn Leu Leu His Glu Ala Asp Ser Ala Val Ala Thr Ala Arg
1               5                   10                  15

Arg Pro Arg

<210> SEQ ID NO 11
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 11

Met Trp Asn Leu Leu His Glu Thr Ala Ser Ala Val Ala Thr Ala Arg
1               5                   10                  15

Arg Pro Arg

<210> SEQ ID NO 12
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 12

Met Trp Asn Leu Leu His Glu Thr Asp Ala Ala Val Ala Thr Ala Arg
1               5                   10                  15

Arg Pro Arg

<210> SEQ ID NO 13
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
```

<223> OTHER INFORMATION: substitution mutant

<400> SEQUENCE: 13

Met Trp Asn Leu Leu His Glu Thr Asp Ser Ala Val Ala Val Ala Arg
1               5                   10                  15

Arg Pro Arg

<210> SEQ ID NO 14
<211> LENGTH: 19
<212> TYPE: PRT
<213> ORGANISM: Artificial Sequence
<220> FEATURE:
<223> OTHER INFORMATION: substitution mutant
<220> FEATURE:
<221> NAME/KEY: misc_feature
<223> OTHER INFORMATION: substitution mutant

<400> SEQUENCE: 14

Met Trp Asn Leu Leu His Glu Ala Asp Ala Ala Val Ala Ala Ala Arg
1               5                   10                  15

Arg Pro Arg

<210> SEQ ID NO 15
<211> LENGTH: 10
<212> TYPE: PRT
<213> ORGANISM: Artificial Sequence
<220> FEATURE:
<223> OTHER INFORMATION: deletion mutant
<220> FEATURE:
<221> NAME/KEY: misc_feature
<223> OTHER INFORMATION: deletion mutant

<400> SEQUENCE: 15

Met Trp Asn Leu Leu Ala Arg Arg Pro Arg
1               5                   10

<210> SEQ ID NO 16
<211> LENGTH: 19
<212> TYPE: PRT
<213> ORGANISM: Artificial Sequence
<220> FEATURE:
<223> OTHER INFORMATION: deletion mutant
<220> FEATURE:
<221> NAME/KEY: misc_feature
<223> OTHER INFORMATION: deletion mutant

<400> SEQUENCE: 16

Ala Ala Ala Ala Ala His Glu Thr Asp Ser Ala Val Ala Thr Ala Arg
1               5                   10                  15

Arg Pro Arg

<210> SEQ ID NO 17
<211> LENGTH: 10
<212> TYPE: PRT
<213> ORGANISM: human

<400> SEQUENCE: 17

Arg Arg Gln Arg Lys Ser Arg Arg Thr Ile
1               5                   10

<210> SEQ ID NO 18
<211> LENGTH: 15
<212> TYPE: PRT
<213> ORGANISM: Artificial Sequence
<220> FEATURE:
<223> OTHER INFORMATION: fusion mutant

```
<220> FEATURE:
<221> NAME/KEY: misc_feature
<223> OTHER INFORMATION: fusion mutant

<400> SEQUENCE: 18

Arg Arg Gln Arg Lys Ser Arg Arg Thr Ile Leu Leu Asn Trp Met
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: fusion mutant
<220> FEATURE:
<221> NAME/KEY: misc_feature
<223> OTHER INFORMATION: fusion mutant

<400> SEQUENCE: 19

Arg Arg Gln Arg Lys Ser Arg Arg Thr Ile Ala Ala Asn Trp Met
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: fusion mutant
<220> FEATURE:
<221> NAME/KEY: misc_feature
<223> OTHER INFORMATION: fusion mutant

<400> SEQUENCE: 20

Arg Arg Gln Arg Lys Ser Arg Arg Thr Ile Leu Ala Asn Trp Met
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: fusion mutant
<220> FEATURE:
<221> NAME/KEY: misc_feature
<223> OTHER INFORMATION: fusion mutant

<400> SEQUENCE: 21

Arg Arg Gln Arg Lys Ser Arg Arg Thr Ile Ala Leu Asn Trp Met
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: fusion mutant
<220> FEATURE:
<221> NAME/KEY: misc_feature
<223> OTHER INFORMATION: fusion mutant

<400> SEQUENCE: 22

Arg Arg Gln Arg Lys Ser Arg Arg Thr Ile Leu Ala Asn Trp Ala
1               5                   10                  15

<210> SEQ ID NO 23
<211> LENGTH: 16
<212> TYPE: PRT
<213> ORGANISM: Artificial Sequence
<220> FEATURE:
```

```
<223> OTHER INFORMATION: fusion mutant
<220> FEATURE:
<221> NAME/KEY: misc_feature
<223> OTHER INFORMATION: fusion mutant

<400> SEQUENCE: 23

Arg Arg Gln Arg Lys Ser Arg Arg Thr Ile Leu Ala Asn Trp Ala Met
1               5                   10                  15

<210> SEQ ID NO 24
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 24

Met Trp Asn Leu Leu
1               5

<210> SEQ ID NO 25
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 25

Met Trp Asn Ala Leu
1               5

<210> SEQ ID NO 26
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 26

Met Ala Asn Leu Leu
1               5

<210> SEQ ID NO 27
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 27

Met Trp Ala Leu Leu
1               5

<210> SEQ ID NO 28
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 28

Leu Leu Asn Trp Met
1               5
```

```
<210> SEQ ID NO 29
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 29

Leu Ala Asn Trp Met
1               5

<210> SEQ ID NO 30
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 30

Leu Leu Asn Ala Met
1               5

<210> SEQ ID NO 31
<211> LENGTH: 5
<212> TYPE: PRT
<213> ORGANISM: Homo sapiens
<220> FEATURE:
<221> NAME/KEY: misc_feature
<223> OTHER INFORMATION: substitution mutant

<400> SEQUENCE: 31

Leu Leu Ala Trp Met
1               5
```

ENDOCYTOTIC PATHWAY DELIVERY VEHICLE FOR TARGETING DRUGS AND ANTIBODIES TO PROSTATE AND OTHER TISSUES

CROSS-REFERENCE TO RELATED APPLICATIONS

This application claims the benefit of U.S. Provisional Application No. 60/615,041, filed on Sep. 30, 2004, which is incorporated by reference herein.

STATEMENT REGARDING FEDERALLY SPONSORED RESEARCH OR DEVELOPMENT

This invention was made with Government support of Grant Nos. DAMD17-02-1-0661 and DAMD17-98-1-8567, awarded by the Army. The Government has certain rights in this invention.

BACKGROUND

1. Field of Invention

This invention relates generally to internalization of membrane proteins and in particular to internalization mediated by a methionine/leucine internalization motif.

2. Related Art

The endocytic pathway includes internalization of the receptor-ligand complex via clathrin-coated pits and accumulation in the endosomes. The receptor-ligand complex then dissociates in the endosomes and the dissociated molecules are either recycled back to the cell surface or targeted to lysosomes for degradation. Targeting of most receptors to coated pits and their traffic through endocytic compartments are generally mediated by endocytic signals located in the cytoplasmic domain of proteins. These signals fall into two major categories, tyrosine-based and di-leucine based signals.

The tyrosine-based signals are represented by NPXY and YXXΦ consensus motifs with the Y residue being critical for their function. NPXY signals mediate internalization of several type-1 membrane proteins such as LDL receptor, epidermal growth factor receptor, insulin receptor and others. The YXXΦ (Φ-bulky hydrophobic side chain) signals mediate internalization and lysosomal targeting of several type I and type II membrane proteins such as transferrin receptor, mannose-6-phosphate receptor, asialoglycoprotein receptor, polymeric immunoglobulin receptor and others.

The di-leucine based signals require two consecutive leucines or a leucine-isoleucine pair for their function. Studies have identified two distinct classes of di-leucine based signals represented by [DE]XXXL[LI] and DXXLL consensus sequences. Both of these signals are involved in internalization and lysosomal targeting of several membrane proteins. Proteins such as CD3-γ, LIMP-II, tyrosinase CD4, GLUT4 have a [DE]XXXL type signal whereas a DXXLL signal has been characterized in mannose 6-phosphate/insulin-like growth factor-II receptor, the cation-dependent mannose-6-phosphate receptor, LDL-receptor related proteins, β-secretase and others.

The membrane protein Prostate Specific Membrane Antigen (PSMA) was originally identified by the monoclonal antibody 7E11-C5 raised against the human prostate cancer cell line LNCaP. Subsequently, the PSMA gene was cloned (Israeli et al., 1993), and mapped to chromosome 11q. PSMA is a type II membrane protein with a short cytoplasmic N-terminal region (19 amino acids), a transmembrane domain (24 amino acids) and a large extracellular C-terminal portion (707 amino acids) with several potential N-glycosylation sites. It has been shown that PSMA is homologous to glutamate carboxypeptidase II (85% at nucleic acid level) isolated from rat brain, has folate hydrolase activity and N-acetylated α-linked acidic dipeptidase (NAALDase) activity. The extracellular domain of PSMA shows homology (26% identity at the amino acid level) to the transferrin receptor I and to a cloned transferrin receptor II.

PSMA has been the subject of interest in cancer research due to its potential as a diagnostic and therapeutic target for human prostate cancer. PSMA is abundantly expressed in prostate cancer cells. Its expression is further increased in higher-grade cancers, metastatic disease, and hormone-refractory prostate carcinoma. In addition, PSMA has become the focus of even more intense interest due to the findings that it is selectively expressed in the neovasculature of nearly all types of solid tumors, but not in the vasculature of normal tissue. The function of PSMA with respect to vascular endothelial cell biology and the direct correlation between its expression and increasing tumor aggressiveness in prostate cancer are intriguing. The use of antibodies against PSMA for immunotherapy of prostate cancer is the subject of research investigation.

The development of new therapeutic agents for the treatment of cancer and other diseases is often limited by an inability of the agents to cross the cell membrane. Size, charge and chemical composition are some of the factors responsible for this inability. Although methods such as liposome delivery and viral delivery, including adenovirus or lentivirus mediated delivery, can potentially provide therapeutic agents to cells, there is a continuing need to develop additional ways to deliver therapeutic agents.

SUMMARY

The present invention concerns chimeric transmembrane proteins containing a novel, internalization motif, and methods of using such proteins. The novel motif is naturally present at the N-terminus of the cytoplasmic tail of PSMA, where it mediates the internalization of this integral membrane protein. Deletion of the cytoplasmic tail abolishes PSMA internalization, while transfer of the motif to the cytoplasmic tail of a non-internalized membrane protein leads to internalization. Thus, the motif can mediate the internalization of an integral membrane protein when located at a cytoplasmic portion of the protein. The motif is a 5 amino acid sequence, and is described herein as the "MXXXL internalization motif", where M represents the amino acid methionine, L represents the amino acid leucine, and X represents any amino acid.

In one aspect, the present invention provides a chimeric transmembrane protein comprising a) a membrane-spanning polypeptide, and b) an internalization motif of the sequence $MX_1X_2X_3L$ or $LX_3X_2X_1M$ connected to the membrane-spanning polypeptide. In the chimeric transmembrane protein, at least a portion of the membrane-spanning polypeptide is heterologous to the internalization motif; $X_1$, $X_2$, and $X_3$ are each independently any amino acid selected from the group consisting of alanine, arginine, asparagine, aspartate, cysteine, glutamine, glutamate, glycine, histidine, isoleucine, leucine, lysine, methionine, phenylalanine, proline, serine, tyrosine, threonine, tryptophan, and valine; the internalization motif occurs at a cytoplasmically located portion of the chimeric transmembrane protein; and the chimeric transmembrane protein is internalized when expressed on the plasma membrane of a mammalian cell or other eukaryotic cell. In preferred embodiments, the internalization motif is located at the N- or C-terminus of the chimeric transmembrane protein, forming a cytoplasmic tail. In another embodiment, an internalization motif, has the sequence $MX_1X_2X_3L$, wherein $MX_1X_2X_3L$ is selected from the group consisting of SEQ ID NO: 24, SEQ ID NO: 25; SEQ ID NO: 26, and SEQ ID NO: 27; or $LX_3X_2X_1M$, wherein $LX_3X_2X_1M$ is selected from the group consisting of SEQ ID NO: 28, SEQ ID NO: 29, SEQ ID NO: 30, and SEQ ID NO: 31.

In another aspect, the present invention also provides a method of modifying a first polypeptide for targeting to endosomes. The method comprises connecting the first polypeptide to a second polypeptide comprising the MXXXL internalization motif to form a chimeric transmembrane protein. The chimeric transmembrane protein is internalized when expressed on the plasma membrane of a mammalian cell or other eukaryotic cell.

The present invention further provides polynucleotides encoding chimeric transmembrane proteins of the present invention, vectors that encode and express chimeric transmembrane proteins, and methods of providing cytotoxic molecules to cells, particularly cancer cells, by means of chimeric transmembrane proteins.

It is contemplated that any composition or method described herein can be implemented with respect to any other composition or method described herein.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF DRAWINGS

FIG. 1 is a schematic representation of PSMA cytoplasmic tail mutants and Tac-PSMA chimera, wherein the partial amino acid sequence of wildtype PSMA (Wt; SEQ ID NO: 1) is shown compared to the partial amino acid sequences of constructs Δcd (SEQ ID NO:2), Ala 4,5 (SEQ ID NO:3), Ala 4 (SEQ ID NO:4), Ala 5 (SEQ ID NO:5), Ala 2 (SEQ ID NO:6), Ala 3 (SEQ ID NO:7), Ala 6 (SEQ ID NO:8), Ala 7 (SEQ ID NO:9), Ala 8 (SEQ ID NO:10), Ala 9 (SEQ ID NO:11), Ala 10 (SEQ ID NO:12), Val 14 (SEQ ID NO:13), Ala 8,10,14 (SEQ ID NO:14), Δ6-14 (SEQ ID NO:15), and MA (5) (SEQ ID NO:16), and the partial amino acid sequence of Tac (Tac Wt: SEQ ID NO:17) is shown compared to the partial amino acid sequences of constructs Tac-MWNLL (SEQ ID NO:18), Tac-MWNAA (SEQ ID NO:19), Tac-MWNAL (SEQ ID NO:20), Tac-MWNLA (SEQ ID NO:21), Tac-AWNAL (SEQ ID NO:22), and Tac-MAWNAL (SEQ ID NO:23);

DETAILED DESCRIPTION

Polypeptides

Figure 2:
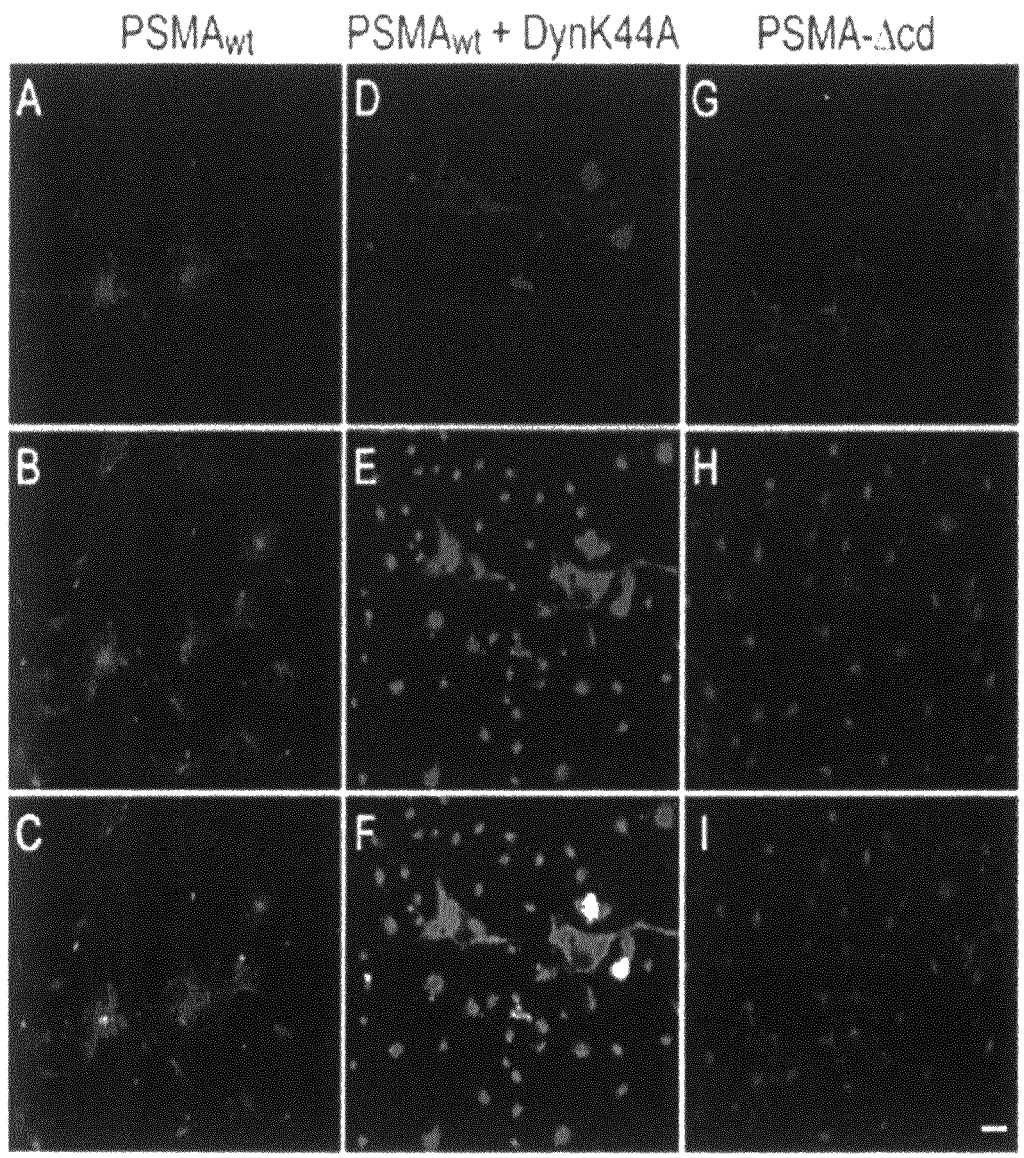
FIGS. 2A-2I provide confocal microscopy images showing PSMA internalization in COS-7 cells expressing wild type PSMA ($PSMA_{wt}$) and a cytoplasmic tail deletion mutant (PSMA-Δcd)

As used herein, the term "polypeptide" or "protein" refers to a polymer in which the monomers are amino acid residues which are joined together through peptide bonds, and is intended to encompass any amino acid sequence. A polypeptide can be a portion of a larger polypeptide; for example, the amino acid sequence of a membrane-spanning polypeptide can be part of the amino acid sequence of a chimeric membrane protein. A polypeptide has at least 2 amino acid residues, and preferably, at least 5 amino acid residues.

In accordance with the present invention, a chimeric transmembrane protein is formed by connecting the MXXXL internalization motif to a heterologous polypeptide. The chimeric transmembrane protein can be described as comprising a membrane-spanning polypeptide and an internalization motif. The MXXXL internalization motif has the amino acid sequence $MX_1X_2X_3L$ or $LX_3X_2X_1M$, written N-terminal to C-terminal in one letter amino acid code, where $X_1$, $X_2$, and $X_3$ are each independently any amino acid.

There term "membrane-spanning polypeptide" refers to any polypeptide that spans the plasma membrane when the chimeric transmembrane protein is expressed in a suitable eukaryotic cell, such as a mammalian cell, and inserted into the plasma membrane. Typical membrane-spanning polypeptides include naturally occurring transmembrane proteins, or integral membrane proteins, present in the plasma membrane of various eukaryotic cells. Membrane-spanning polypeptides also include proteins such as viral envelope proteins that are produced on the surface of eukaryotic cells during the course of viral infection, and integral membrane proteins of mitochondria that are found in organelles within eukaryotic cells. Other types of membrane-spanning polypeptides include artificial polypeptides such as substitutional, deletion or insertion variants derived from naturally occurring integral membrane proteins, and transmembrane proteins containing artificially designed transmembrane regions. Fusion proteins containing sequences derived from a transmembrane protein fused to functional sequences, such as an antibody epitope to facilitate purification of the chimeric protein, an active site from an enzyme to facilitate detection of the chimeric protein, a linker or spacer peptide to provide proper spacing of the internalization motif from the membrane-spanning protein, a signal sequence for proper insertion into the plasma membrane, and other functional sequences, are also considered membrane-spanning polypeptides.

A list of representative integral membrane proteins that can be incorporated into the present invention include: a) tyrosine kinase receptors such as VEGF, EGR, insulin, IGF-1, PDGF, NGF, and FGF receptors; b) the α-subunit of G-protein coupled receptors such as the calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsin and odorant receptors; c) subunits of ionotropic receptors such as the acetylcholine, glycine, Gaba(A,), glutamate and glycine receptors; d) subunits of integrin receptors; and e) integral membrane proteins such as the LDL receptor, prostaglandin $H_2$ synthase, CD3-γ, LIMP-II, tyrosinase, CD4, calcium ATPase, GLUT4, and the Na, K-ATPase α-subunit.

The term "chimeric transmembrane protein" refers to a transmembrane protein that contains two or more subsequences that do not naturally occur in the same relationship to each other. Similarly, a polypeptide or portion of a polypeptide is "heterologous" to the MXXXL internalization motif when the amino acid sequence of the polypeptide or portion of the polypeptide is not naturally found in the same relationship to the internalization motif. For example, although a non-internalized membrane protein may have the sequence MXXXL within its polypeptide chain, the sequence does not naturally occur at the N-terminus or C-terminus of the protein. Thus, placing the MXXXL internalization motif at one end of the protein produces a chimeric transmembrane protein having a polypeptide sequence that is heterologous to the internalization motif. Similarly, an insertional variant has an additional amino acid sequence that is not naturally present in the native protein, and a substitution variant has an amino acid residue that is not naturally present in the native protein. Both variants contain a sequence that is heterologous to the polypeptide sequence of the native protein.

A transmembrane protein can be characterized as a single-pass transmembrane protein having a polypeptide chain that passes once through a cell membrane, or a multipass transmembrane protein having a polypeptide chain that passes through a cell membrane more than once. Examples of single-pass transmembrane proteins include receptors such as the LDL receptor, epidermal growth factor receptor, and insulin receptor, and membrane proteins such as CD3-γ, LIMP-II, and tyrosinase and CD4. Examples of multipass transmembrane proteins include the Na, K-ATPase α-subunit, calcium ATPase, the α-subunit of G-protein coupled receptors, and GLUT4. The term "transmembrane region" refers to a hydrophobic, membrane-spanning section of a polypeptide chain.

In accordance with the present invention, the MXXXL internalization motif is located at a cytoplasmic terminus, side or portion of the chimeric transmembrane protein. When used to describe the structure of a polypeptide, the term "cytoplasmic" refers to an end or part of the protein that is located in the cytoplasm when the protein is expressed on the plasma membrane. The cytoplasmic terminus, side or portion can also be characterized as "intracellularly" located.

A transmembrane protein is typically synthesized with a signal sequence at the N-terminus for association with the signal recognition particle (SRP) and the rough endoplasmic reticulum. With a type I protein, the signal sequence is cleaved by a peptidase located in the lumen of the rough endoplasmic reticulum, exposing a new N-terminus, and the transmembrane protein's final configuration has a cytoplasmically located C-terminus and an extracellular N-terminus. As such, in accordance with the present invention, the MXXXL internalization motif is located at the C-terminus of a chimeric transmembrane protein that is in a type I configuration. With a type II protein, the signal sequence remains intact and the transmembrane protein has a final configuration with the N-terminus cytoplasmically located and the C-terminus extracellular. In chimeric transmembrane proteins having a type II configuration, the MXXXL internalization motif is located at the N-terminus of the polypeptide, usually as part of the signal sequence. With a type III protein, the signal sequence remains intact, with the N-terminus extracellular and the C-terminus cytoplasmically located in the final configuration. In type III chimeric transmembrane proteins, the MXXXL internalization motif is located at the C-terminus of the chimeric protein. In multipass chimeric transmembrane proteins, the MXXXL internalization motif can be located at the C-terminus, N-terminus or cytoplasmic loop of the protein depending on which parts of the protein are located in the cytoplasm.

The MXXXL internalization motif can be present in a chimeric transmembrane protein in either the $MX_1X_2X_3L$ or $LX_3X_2X_1M$ orientation. For example, a type I or type III chimeric transmembrane protein can have either the sequence $MX_1X_2X_3L$ or the sequence $LX_3X_2X_1M$ at its C-terminus. Similarly, a type II chimeric transmembrane protein can have either the $MX_1X_2X_3L$ sequence or the $LX_3X_2X_1M$ sequence at its N-terminus. In preferred embodiments, the $LX_3X_2X_1M$ sequence is positioned at the cytoplasmically located C-terminus of a type I and type III chimeric transmembrane protein, and the $MX_1X_2X_3L$ sequence is positioned at the cytoplasmically located N-terminus of a type II chimeric transmembrane protein. Similarly, any chimeric transmembrane protein whose N-terminus is located in the cytoplasm preferably has the $MX_1X_2X_3L$ sequence at the N-terminus, while any chimeric transmembrane protein whose C-terminus is located in the cytoplasm preferably has the $LX_3X_2X_1M$ sequence at the C-terminus.

The chimeric transmembrane protein comprises a membrane-spanning polypeptide and an MXXXL internalization motif. In accordance with the present invention, at least a portion of the membrane-spanning polypeptide is heterologous to the internalization motif. The heterologous portion can comprise an amino acid sequence obtained or derived from an integral membrane protein, which can be a non-internalized integral membrane protein. Also, the heterologous portion can contain at least one transmembrane region. Alternatively, in other embodiments, the heterologous portion can lack a transmembrane region, or can contribute a part of a transmembrane region.

Further, the membrane-spanning polypeptide can have an amino acid sequence that is obtained or derived from an integral membrane protein, which can be a non-internalized integral membrane protein. In addition, the membrane-spanning polypeptide can comprise an amino acid sequence derived from two or more proteins. In preferred embodiments, the entire amino acid sequence of the membrane-spanning polypeptide is heterologous to the internalization motif. In other embodiments, the chimeric transmembrane protein consists of the internalization motif connected to a membrane spanning polypeptide obtained or derived from an integral membrane protein, which is preferably a naturally occurring integral membrane protein.

Polypeptides, or polypeptide sequences, obtained from a transmembrane protein have amino acid sequences which are the same as the amino acid sequences present in the transmembrane protein. Polypeptides, or polypeptide sequences, derived from a transmembrane protein can be substitutional, insertional or deletion variants of the transmembrane protein, as long as the derivatives do not prevent plasma membrane insertion and internalization of chimeric membrane proteins. Deletion variants lack one or more residues of the native protein that are not essential for protein stability or membrane localization. Insertional variants typically involve the addition of material at a non-terminal point in the polypeptide. This may include, for example, the insertion of an immunoreactive epitope or simply a single residue.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

According to the present invention, the chimeric transmembrane polypeptides are expressed in eukaryotic cells. As such, the amino acids residues incorporated into the polypeptide are typically the 20 common amino acids naturally synthesized in proteins. Thus, reference to the MXXXL internalization motif, where X can be any amino acid, is understood to mean that X of the sequence can be any of the 20 common amino acids.

Nucleic Acids

The term "polynucleotide" refers to both DNA and RNA, and the term "nucleotide sequence" includes both DNA and RNA sequences. For example, the nucleotide sequence of a transmembrane protein includes the gene encoding the native protein, its complementary DNA, and the RNA corresponding to the foregoing; also included are messenger RNA encoding for the transmembrane protein, its complementary RNA, and the DNA corresponding to the foregoing.

The chimeric transmembrane proteins of the present invention can be prepared by molecular biological and recombinant nucleic acid methods standard in the art. DNA molecules encoding the internalization motif or a membrane spanning polypeptide can be derived from cloned sequences or by chemical synthesis. A DNA fragment encoding a chimeric transmembrane protein can be included as part of an expression vector for the production of protein in eukaryotic cells. The term "expression vector" refers to any type of genetic construct comprising a nucleic acid encoding for an RNA capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, an expression vectors may contain nucleic acid sequences that serve other functions as well and are described infra. A variety of expression vectors are known in the art, and many are commercially available. Expression vectors are preferably purified and/or isolated before use.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment. The promoter may be heterologous or endogenous.

Tables 1 and 2 list several elements/promoters which may be employed, in the context of the present invention, to regulate the expression of a transgene. This list is not exhaustive of all the possible elements involved but, merely, to be exemplary thereof.

TABLE 1

| PROMOTER |
|---|
| Uroplakin II |
| Probasin |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DR☐ |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |

TABLE 1-continued

| PROMOTER |
| --- |
| $\alpha_{1\text{-}Antitrypsin}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | Poly(rI)X |
|  | Poly(rc) |
| Adenovirus 5 E2 | Ela |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone ☐ Gene | Thyroid Hormone |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, a polyadenylation signal is typically included to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

In order to propagate a vector in a host cell, it may contain one or more origins of replication sites (often termed "ori"), which is a specific nucleic acid sequence at which replication is initiated.

Expression of Chimeric Transmembrane Proteins

A host cell for expression of chimeric proteins can include a eukaryotic cell in culture, or a cell found in a tissue, organ or body of a subject. Examples of eukaryotic host cells for replication and/or expression of a vector in culture include HeLa, NIH3T3, Jurkat, 293, COS, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Alternatively, expression of a chimeric transmembrane protein in cells can be achieved by means of RNA transfection, whereby a translatable RNA encoding the chimeric membrane protein is introduced into the cells and translated to produce the chimeric transmembrane protein. Such RNAs can be prepared using standard molecular biology and recombinant nucleic acid methodologies.

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells. The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus, adeno-associated virus (AAV) and herpesviruses may be employed. The construction and use of these viral vectors is well known in the art.

In preferred embodiments, expression vectors encoding chimeric transmembrane proteins are introduce into host cells via liposomes. A liposome is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Cationic liposomes, made with cationic lipids such as DOTMA, DOSPA, and DMRIE, form complexes with DNA. These complexes bind to the surface of cells and internalize to endosomes, where the DNA is released for transcription. The preparation and use of DNA/liposome complexes for delivery of expression vectors into eukaryotic cells is well known, and lipids for liposome preparation are commercially available (for example, from Invitrogen Corp., Carlsbad, Calif.). Similarly, RNA/liposome complexes can be utilized to introduce translatable RNA molecules into cells.

Administering DNA/liposome complexes to cells in a patient or subject generally involves contacting target cells, such as tumor cells, with the complex. The routes of administration will vary, naturally, with the location and nature of the lesion, and can include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

Delivery of Cytotoxic Agents

The present invention further provides a method of providing a cytotoxic agent to a cell. The cell is preferably a cancer cell, and more preferably a prostate cancer cell or a bladder cancer cell. The method comprises expressing a chimeric transmembrane protein of the present invention in the plasma membrane of the cancer cell, then administering an antibody conjugated to a cytotoxic agent. The antibody is designed to recognize an epitope on the extracellular surface of the chimeric transmembrane protein. After binding of the antibody conjugate to the chimeric protein, the chimeric protein internalizes, bringing the antibody conjugate inside the cell. The cytotoxic moiety can then express its cytotoxic activity. One advantage of this method is that potentially any antibody that recognizes the extracellular portion of a non-internalized transmembrane protein can be utilized by adding the MXXXL internalization motif to the non-internalized transmembrane protein and targeting the chimeric protein with the antibody. Thus, the method can be practiced with a wider array of antibodies than previous methods using immunotoxins. Another advantage is that the cytotoxic agent has potentially less side effects since it can be selectively internalized in target cells.

The cytotoxic agent can be provided to any cells whose destruction is warranted, and in particular, to hyperproliferative cells, which can be a prostate, bladder, blood, bone, bone marrow, brain, breast, colon, esophagus, gastrointestine, gum, head, kidney, liver, lung, nasopharynx, neck, ovary, skin, stomach, testis, tongue, or uterus cell. In some embodiments of the invention, the hyperproliferative cell being targeted is a vascular cell, such as an endothelial cell which include but is not limited to vascular smooth muscle cells, and atherosclerosis and post-angioplasty restenosis. The cell can be in a human or other mammal.

In accordance with the present invention, the antibody can be a polyclonal or monoclonal antibody, or derivatives thereof, including a chimeric, humanized or human antibody. The antibody can be an entire immunoglobulin or antibody or any functional fragment of an immunoglobulin molecule, or combinations thereof, as long as the protein binds to the target chimeric transmembrane protein. Examples of such functional entities include complete antibody molecules, antibody fragments, such as Fv, single chain Fv, complementarity determining regions (CDRs), $V_L$ (light chain variable region), $V_H$ (heavy chain variable region), Fab, F(ab')$_2$, and any combination of those or any other functional portion of an immunoglobulin peptide capable of binding to the target chimeric protein. Methods of producing such antibody related molecules are well known in the art, and are discussed in U.S. Pat. No. 6,824,780, incorporated by reference herein.

The term "cytotoxic agent" as used herein refers to a substance that inhibits or prevents the function of cells and/or causes destruction of cells. The term is intended to include radioactive isotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents such as methotrexate, adriamicin, vinca alkaloids (vincristine, vinblastine, etoposide), doxorubicin, melphalan, mitomycin C, chlorambucil, daunorubicin and other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof.

In general, depending on the particular cytotoxic agent, conjugates of an antibody and a cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dim ethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) and N-succinimidyl-4-(2-pyridylthio)pentanoate (SPP) to provide for a disulfide linkage.

A radioactive agent may be incorporated in the conjugate in known ways. For example, the peptide may be biosynthesized or may be synthesized by chemical amino acid synthesis using suitable amino acid precursors. Agents such as $Re^{186}$, $Re^{188}$ can be attached via a cysteine residue in a peptide. The IODOGEN method can be used to incorporate iodine-123.

Alternatively, a fusion protein comprising the antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

Therapeutic formulations of the antibodies used in accordance with the present invention can be prepared for storage by mixing an antibody having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as polyethylene glycol (PEG).

As is apparent, the formulation may contain more than one antibody-conjugate. The antibody can be directed to the same or different chimeric membrane proteins, depending on the number and type of different chimeric membrane proteins expressed on the surface of the target cells.

In practice, an expression vector encoding a chimeric transmembrane protein of the present invention, under the control of a promoter active in the target cells, can be administered to the cells as a DNA/liposome complex. This can be performed, for example, by directly applying the DNA/liposome complex to tumor cells in a subject. After allowing time for the chimeric transmembrane protein to be expressed on the plasma membrane of the tumor cells, an antibody that recognizes an epitope on the extracellular portion of the chimeric protein can be conjugated to a cytotoxic agent and administered to the cells. Binding of the antibody conjugate to the chimeric transmembrane protein followed by internalization results in delivery of the toxic agent to the inside of the target cells.

The present invention may be better understood by referring to the accompanying examples, which are intended for illustration purposes only and should not in any sense be construed as limiting the scope of the invention as defined in the claims appended hereto.

Example 1

Experimental Procedures

Plasmid Constructs

Cloning and characterization of full-length cDNA of PSMA was described earlier (Israeli et al., 1993). The alanine scan mutagenesis approach was utilized to mutate each of the cytoplasmic tail amino acids in the cytoplasmic tail of PSMA. Alanine scan mutagenesis was essentially carried out by polymerase chain reaction (PCR) using sense primers carrying respective mutation of the cytoplasmic tail amino acid (positions 2-15) to alanine. A Kozak consensus sequence (GCCACC) and a translation start site (ATG) were incorporated at the N-terminus of the sense primers. A cytoplasmic tail deletion mutant of PSMA was created by deleting the N-terminal 15 amino acids using polymerase chain reaction (PCR). An alanine and three arginine residues proximal to the transmembrane domain were retained since these three arginine residues may be necessary to maintain the type II orientation of the protein. Also, PSMA constructs in which the cytoplasmic tail amino acids 6-14 were deleted or all the three putative phosphorylation sites were mutated (PSMA-T8A/S10A/T14A) and a PSMA construct containing five alanines inserted after the start codon [PSMA-MA(5)] were generated using PCR. Tac-PSMA chimera were also generated using PCR. Full-length Tac was described earlier (Leonard et al., 1984). Tac cytoplasmic tail chimera containing the di-leucine like motif of PSMA (Tac-MWNLL), di-leucine motif mutated to alanine (Tac-MWNAA), leucine at position 5 mutated to alanine (Tac-MWNLA), leucine at position 4 mutated to alanine (Tac-MWNAL), methionine at first position mutated to alanine in Tac with leucine at position 4 mutated to alanine (Tac-AWNAL), and with an extra alanine (Tac-MAWNAL) were generated. Since Tac is a type I membrane protein, to have the N-terminal methionine free as in PSMA we used primers encoding the respective amino acids in the reverse orientation. Full-length PSMA [designated as wild type PSMA ($PSMA_{wt}$)], cytoplasmic tail mutants of PSMA, and Tac-PSMA chimeras were inserted into eukaryotic expression vector pCDNA3 (Invitrogen Corporation, Carlsbad, Calif.). The mutations were verified by DNA sequencing.

Constructs utilized in this study are shown in FIG. 1. Deletions are shown by horizontal arrows and insertion of additional alanines are indicated. Amino acids converted to alanine or valine are indicated as A and V, respectively. Internalization (INT) positive (+) or negative (−) for the respective constructs is indicated.

Cell Culture and Transfection

COS-7 cells (ATCC CRL 1651) were grown in DMEM supplemented with 10% fetal bovine serum containing streptomycin and penicillin at 5% $CO_2$ in a water-saturated atmosphere. Cells grown on glass coverslips were transiently transfected by the calcium phosphate method as described earlier (Rajasekaran et al., 1994). After transfection (48 hours) the cells were tested for the uptake of antibodies as described below. HeLa cells expressing hemagglutinin-tagged D176A/W421A mutant μ2 constructs under the control of a tetracycline-repressible promoter have been described earlier (Nesterov et al., 1999). The cells were grown in DMEM supplemented with 10% fetal bovine serum containing streptomycin and penicillin, 400 μg/ml G418, 200 ng/ml puromycin, and 10 ng/ml doxycycline at 5% $CO_2$ in a water-saturated atmosphere. Cells plated on glass coverslips were used for transient transfection by the calcium phosphate method. 12 hours after transfection expression of the mutant μ2 protein was induced by replacing the culture medium with doxycyline-free medium. 8 hours before the planned experiments sodium butyrate was added to the culture medium to ensure high expression levels of the mutant μ2 protein to replace the endogenous wildtype μ2 in AP-complexes. Transfected cells were used 60 hours after transfection.

Antibody Uptake and Immunofluorescence Analysis

Antibody uptake was carried out as described previously (Liu et al., 1998). In brief, the cells were washed with DMEM containing 0.5% fatty acid free BSA (DMEM-BSA) and incubated at 37° C. for 2 hours with mAb J591 (5 μg/ml). Cells were then fixed, permeabilized and incubated with Texas-Red conjugated secondary antibody (Jackson Immunoresearch, West Grove, Pa.). To visualize PSMA localization in endosomes, cells were co-incubated with FITC-conjugated transferrin (Jackson Immunoresearch, Westgrove, Pa.) during J591 incubation. To monitor the internalization of Tac-PSMA chimera, monoclonal antibody against the extracellular domain of Tac, 7G7 (Rubin et al., 1985) was utilized. For kinetic analysis of PSMA uptake the cells were incubated with J591 and FITC-conjugated transferrin for 1 hour at 4° C., washed three times and then incubated in DMEM at 37° C., 5% $CO_2$ to allow for uptake. The cells were fixed at the indicated timepoints and incubated with Texas-Red conjugated secondary antibody. Uptake of antibodies (mAbs J591 and 7G7) and transferrin were visualized and quantitated by confocal microscopy (see below). To visualize surface expression of PSMA and Tac-PSMA chimeras, COS cells transfected with the respective plasmid were fixed and stained with mAb J591 and 7G7, respectively, under non-permeabilized conditions.

Confocal Microscopy

Co-distribution of internalized mAbs J591 or 7G7 and transferrin were examined using a Fluoview laser scanning confocal microscope (Olympus America Inc, Melville, N.Y.). To detect simultaneously FITC- and Texas red-labeled antigens, samples were excited at 488 and 568 m with Argon and Krypton lasers, respectively, and the light emitted between 525-540 nm was recorded for FITC and above 630 nm for Texas red. Images were generated using Fluoview software (version 2.1.39). 30-40 transfected cells were examined for each transfection done in duplicate and the representative data are shown.

Quantification of internalization in COS cells expressing $PSMA_{wt}$ and PSMA harboring mutation of the fourth leucine (PSMA-L4A) or fourth and fifth leucine (PSMA-L4A/L5A) was done using image analysis software (Fluoview, version 2.1.39). Average pixel intensities of internalized transferrin (green) and mAb J591 (red) from optical sections of 30-40 cells were determined. Since the transferrin uptake was more or less uniform, PSMA internalization was normalized to transferrin uptake. An analysis of variance was used to compare the PSMA/transferrin ratios as a function of time between $PSMA_{wt}$ and PSMA-L4A. A logarithmic transform was used to stabilize variance and for computing 95% confidence intervals for the geometric mean of PSMA-L4A mutant ratios as a percentage of $PSMA_{wt}$ ratios.

N-Acetylated α-Linked Acidic Dipeptidase (NAALDase) Activity

NAALDase activity was determined as described by (Sekiguchi et al., 1989). COS cells were transfected with $PSMA_{wt}$ on 60 mm culture dishes. After 48 hours of transfection, cells were incubated with 1 μCi/ml $^3$H-NAAG (NEN, Boston, Mass.) in Krebs-Ringer bicarbonate medium or in Dulbecco's modified eagle medium for 1 hour. The medium was removed and the cells were washed three times with their respective incubation medium. Cells were then lysed in 1% Triton-X-100 and the radioactivity was determined using a scintillation counter (Beckman LS 6500). Counts were normalized to protein. Protein concentrations of the cell lysates were determined using the BioRad DC reagent (BioRad Laboratories, Hercules, Calif.) according to manufacturer's instructions.

Example 2

Internalization of Prostate Specific Membrane Antigen Mediated by MXXXL Motif

To study the internalization of PSMA, COS cells were transiently transfected with $PSMA_{wt}$ cDNA (FIG. 1) and uptake of mAb J591 was monitored by immunofluorescence and confocal microscopy. The internalized antibody showed a distinct spot-like staining pattern at the perinuclear region (FIG. 2A). This spot-like staining is reminiscent of the recycling endosomal compartment and internalized transferrin, a marker for this compartment, co-localized with endocytosed PSMA (FIGS. 2A, B, and C) indicating that PSMA is localized to the recycling endosome. We have shown earlier that PSMA is internalized via clathrin-coated vesicles in LNCaP cells (Liu et al., 1998). To further confirm that PSMA is internalized via a clathrin-dependent endocytic mechanism in COS cells we tested whether PSMA is internalized in cells expressing a GTPase-deficient dynamin mutant (K44A) which is known to inhibit clathrin-dependent endocytosis in cultured cells. In these cells internalization of PSMA was not detected (FIGS. 2D, E, and F) further confirming that PSMA is internalized via a clathrin-dependent endocytic pathway.

To test whether the cytoplasmic tail of PSMA contains a signal that mediates its internalization the PSMA cytoplasmic tail was deleted and the mutant (PSMA-Δcd) was expressed in COS cells. PSMA-Δcd was clearly expressed on the cell surface as revealed by immunofluorescence staining under non-permeabilized condition (our unpublished results). Incubation of these cells with mAb J591 did not show uptake or localization to the endosomes and internalized transferrin did not reveal a co-distribution with PSMA (FIGS. 2G, H and I) indicating that the cytoplasmic tail of PSMA contains a signal that mediates its internalization.

In FIG. 2, COS cells transiently transfected with $PSMA_{wt}$ were simultaneously incubated with mAb J591 (A) and FITC-transferrin (B) for 2 hrs, washed, fixed in cold methanol and stained with Texas-red conjugated anti-mouse antibody. Representative medial optical sections are shown. FIG. 2C is a merged image. A yellow color indicates the co-distribution of FITC-transferrin and internalized PSMA. (D-F) COS cells expressing Dynamin K44A and $PSMA_{wt}$ cDNA were incubated with mAb J591 for 2 hrs, washed fixed, and stained with FITC-conjugated anti-mouse antibody to detect PSMA (D)

and with polyclonal anti-dynamin antibody and Texas-red conjugated anti-rabbit antibody to detect cells expressing the dynamin mutant (E). FIG. 2F is a merged image. Note that in cells expressing DynaminK44A, PSMA was not internalized. (G–I) PSMA-Δcd expressing cells were incubated with mAb J591 (G) and FITC-transferrin (H) as described above. PSMA-Δcd does not internalize and therefore, does not co-localize with internalized transferring (I). In the figure, Bar=5µ.

The cytoplasmic tail of PSMA contains two consecutive leucines as reported for di-leucine-like motifs (FIG. 1). To examine whether this motif functions as an internalization signal for PSMA, the di-leucine pair was converted to di-alanine (PSMA-L4A/L5A), the mutant protein was expressed in COS cells and uptake of mAb J591 was monitored. The di-alanine mutant of PSMA was clearly expressed on the cell surface as revealed by staining with mAb J591 under non-permeabilized condition (FIG. 3A). Our internalization assay revealed that mAb J591 was not internalized in cells expressing the di-alanine mutant of PSMA (FIG. 3B) and did not show co-distribution with the internalized FITC-transferrin (FIGS. 3C and D) indicating that mutation of the di-leucine pair in the cytoplasmic tail of PSMA abrogates its internalization. We then examined whether both these leucines are essential for the internalization of PSMA. For this purpose single leucine residues at positions 4 (PSMA-L4A) and 5 (PSMA-L5A) were mutated to alanine and the uptake of mAb J591 was studied. Both these mutants were expressed on the cell surface as revealed by staining with mAb J591 under non-permeabilized condition (FIGS. 3E and I). J591 was clearly internalized in cells expressing PSMA-L4A (FIG. 3F) and internalized transferrin (FIG. 3G) co-distributed with the internalized mAb J591 (FIG. 3H). By contrast, in cells expressing PSMA-L5A, mAb J591 was not internalized (FIG. 3J) and the antibody primarily stained the plasma membrane similar to cells expressing PSMA-L4/L5 (FIG. 3B). In these cells co-localization of PSMA and internalized FITC-transferrin was not detected (FIGS. 3K and L). These results indicated that the fifth leucine in the cytoplasmic tail of PSMA is crucial for its internalization.

Figure 3:
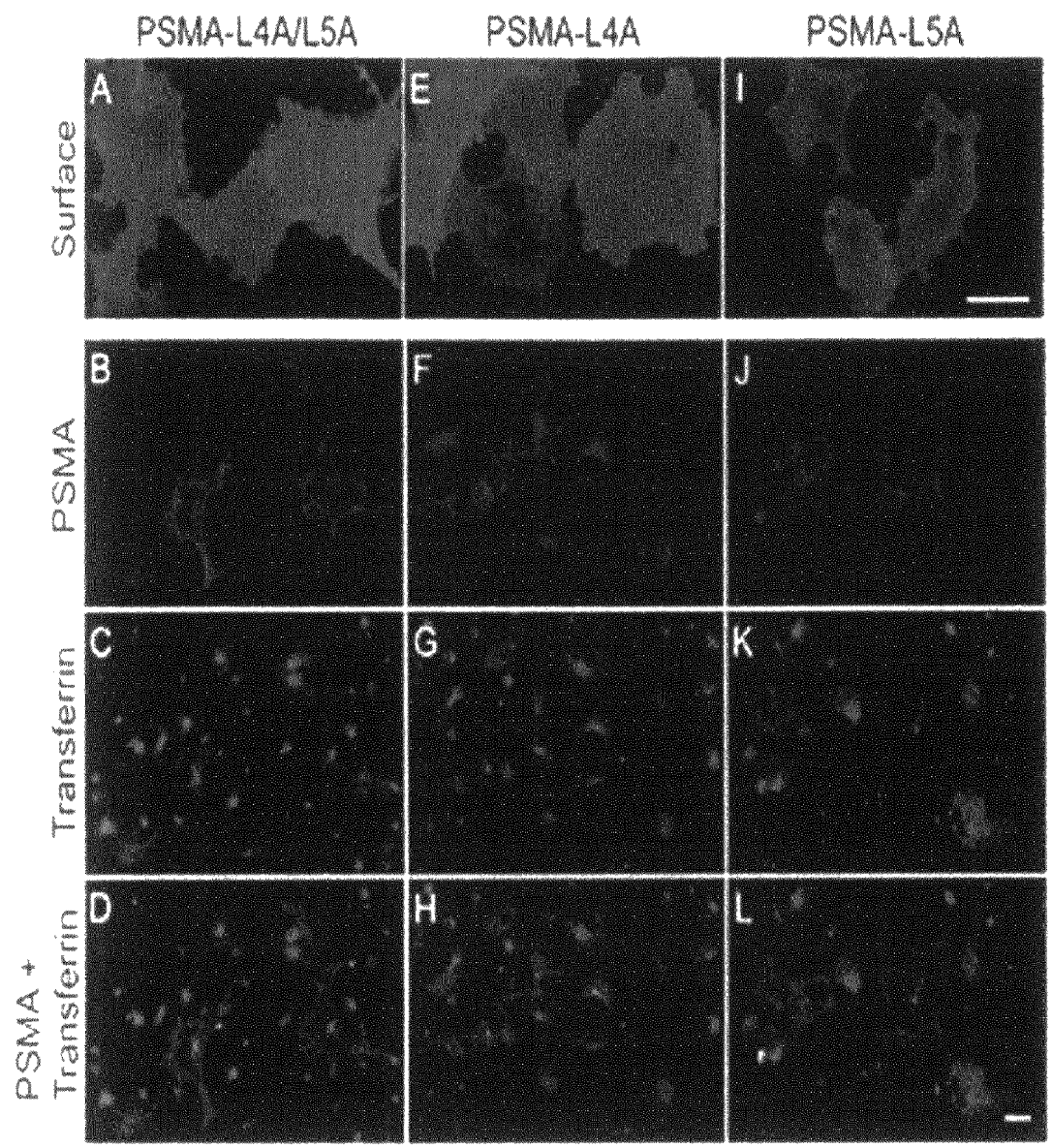
FIGS. 3A-3L provide confocal microscopy images showing internalization of the cytoplasmic tail di-leucine mutants of PSMA.

In FIG. 3, the cells were fixed in paraformaldehyde under non-permeabilized conditions and labeled with mAb J591 followed by FITC-conjugated anti-mouse antibody, then visualized by epifluorescence microscopy. FIGS. 3B, F and J show internalization of PSMA mutants. FIGS. 3C, G and K show FITC-transferrin uptake. FIGS. 3D, H and L are merged images of PSMA and FITC-transferrin. Representative medial optical sections are shown. A yellow color in H indicates the co-distribution of FITC-transferrin and internalized PSMA. In the figure, Bars=10µ (A, E, and I) and 5µ (B, C, D, F, G, H, K, and L).

Figure 4:
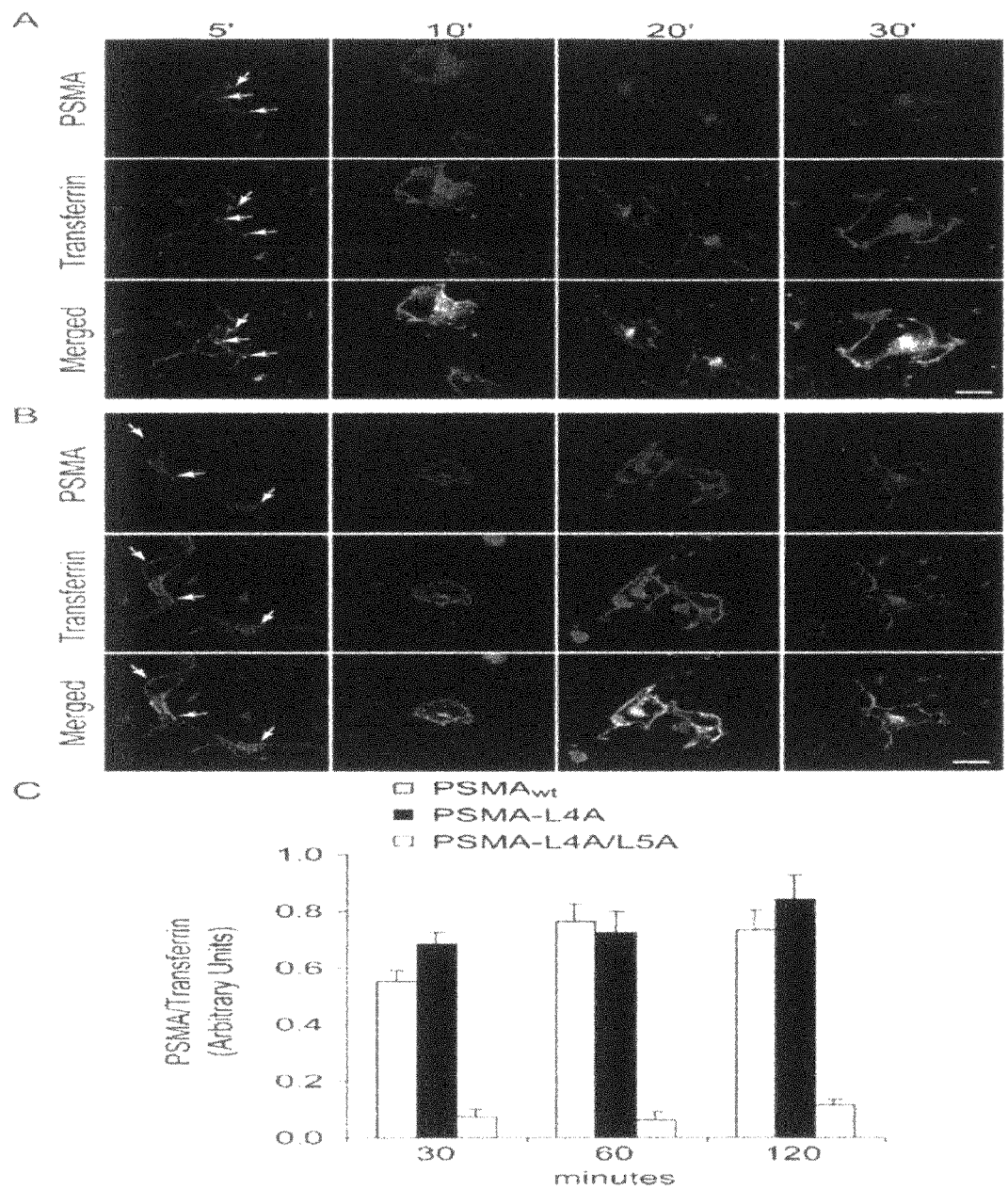
FIGS. 4A-4C provide confocal microscopy images showing a kinetic analysis of internalization of $PSMA_{wt}$ and PSMA-L4A in COS cells.

Since PSMA-L4A was internalized similar to PSMA$_{wt}$ we determined the kinetics of PSMA uptake in cells expressing these constructs. Our efforts to obtain quantitative data using iodinated mAb J591 were not successful since mAb J591 bound to the cell surface was not quantitatively released after acid wash procedures commonly used to release bound antibody on the cell surface. Therefore, we used immunofluorescence and confocal microscopy approaches to determine the kinetics of mAb J591 uptake in cells expressing PSMA$_{wt}$ and PSMA-L4A. As shown in FIG. 4, both PSMA$_{wt}$ and PSMA-L4A expressing cells internalized PSMA rapidly. After five minutes incubation both PSMA and transferrin showed predominant plasma membrane localization with small amounts localized to peripheral vesicles (arrow). Similarly, after 10 minutes PSMA and transferrin co-distributed in more peripheral vesicles while after 20 minutes it accumulated in the REC. Cells expressing PSMA-L4A (FIG. 4B) showed a similar internalization pattern. These results indicated that mutation of the fourth leucine in the cytoplasmic tail of PSMA has a minimal effect on the internalization of PSMA in COS cells. To obtain quantitative data we determined the average pixel intensity represented by internalized PSMA and transferrin using image analysis software (Fluoview, version 2.1.39). Since quantification of internalized PSMA and transferrin was more reliable after 30 minutes we quantified internalized PSMA in cells expressing PSMA$_{wt}$ and PSMA-L4A at 30, 60, and 120 min. We used internalized transferrin as an internal control for defining the area representing the internalized PSMA. Comparison of the internalization kinetics of PSMA$_{wt}$ and PSMA-L4A revealed that PSMA-L4A is internalized with kinetics similar to PSMA$_{wt}$ (FIG. 4C). An analysis of the variance demonstrated that internalization increased with time (P=0.04) but there was no statistical difference between the internalization profiles for PSMA$_{wt}$ and PSMA-L4A mutants (P>0.2). 95% confidence intervals for PSMA-L4A mutant internalization (as percent of PSMA$_{wt}$) were 100-148% at 30 min, 72-116% at 60 min, and 89-143% at 120 min indicating that mutation of the fourth leucine does not alter the internalization properties of PSMA.

FIGS. 4A and B show the time course for internalization of PSMA$_{wt}$ (A) and PSMA-L4A (B). Transiently transfected COS cells were incubated with mAb J591 and FITC-transferrin for the indicated time points and stained with Texas red-conjugated anti-mouse antibody. Representative medial optical sections are shown. Arrows indicate peripheral vesicles containing PSMA and transferrin. In the figure, Bar=5µ. In FIG. 4C, COS cells expressing PSMA$_{wt}$, PSMA-L4A, or PSMA-L4A/L5A were incubated with J591 and FITC-conjugated transferrin for 1 hour at 4° C., washed, and incubated at 37° C. to allow for uptake. The cells were fixed after 30, 60, and 120 min and incubated with Texas-Red conjugated secondary antibody. Uptake of mAbs J591 and transferrin were visualized and quantitated by confocal microscopy. PSMA internalization was normalized to transferring uptake. The bars indicate standard error of 30-40 cells analyzed for each condition.

To further test whether amino acid residues other than the fifth leucine are essential for the internalization of mAb J591 we systematically mutated each of the cytoplasmic tail amino acids into alanine. These point mutations did not affect the internalization of mAb J591 (our unpublished results). Moreover, the construct in which amino acids 6-14 were deleted (PSMA□6-14) internalized mAb J591 when expressed in COS cells. These results demonstrated that the N-terminal first five amino acids in the cytoplasmic tail of PSMA are sufficient to mediate PSMA internalization and the fifth amino acid leucine is crucial for its internalization activity.

Example 3

Transfer of MXXXL Motif to Non-Internalized Tac Protein Leads to Tac Internalization To further confirm that this five amino acid motif of PSMA is sufficient for internalization, we transferred the five N-terminal amino acids of PSMA to the non-internalized protein Tac, a type I membrane protein (Letourneur and Klausner, 1992). Internalization of Tac was monitored by uptake of mAb 7G7 raised against the extracellular domain of Tac (Rubin et al., 1985). In non-permeabilized COS cells, wild type Tac (Tac$_{wt}$) showed a distinct plasma membrane localization (FIG. 5A) indicating that this protein is targeted to the plasma membrane, but incubation with mAb 7G7 did not result in the internalization of this antibody, confirming that Tact is not internalized in COS cells (FIG. 5B) as reported earlier (Letourneur and Klausner, 1992). Co-distribution of mAb 7G7 staining and internalized transferrin was not detected in these cells (FIGS. 5C and D). By contrast, incorporation of the amino acids MWNLL into the Tac cytoplasmic tail (Tac-MWNLL) resulted in the internalization of mAb 7G7 (FIG. 5F). The internalized antibody clearly co-localized with internalized FITC-transferrin (FIGS. 5G and H) indicating that the N-terminal five amino acids in the cytoplasmic tail of PSMA are transferable and are sufficient to confer internalization properties to a non-internalized protein.

FIGS. 5A and E show surface expression of Tac. 48 hrs after transfection. The cells were fixed in paraformaldehyde under non-permeabilized condition, labeled with mAb 7G7 followed by FITC-conjugated anti-mouse antibody and visualized by epifluorescence microscopy. FIG. 5B-D and FIG. 5F-H show internalization of Tac and FITC-transferrin. The cells were incubated with mAb 7G7 and FITC-transferrin for 2 hrs, washed, fixed in cold methanol and stained with Texas-red conjugated anti-mouse antibody. Representative medial optical sections are shown. FIGS. 5B and F show internalization of Tac antibody. FIGS. 5C and G show uptake of FITC-transferrin. FIGS. 5D and H are merged images. A yellow color in H indicates the co-distribution of FITC-transferrin and internalized Tac. In the figure, Bars=10µ (A, E) and 5µ (B, C, D, F, G, and H).

In cells expressing Tac-MWNAA where the two consecutive leucines are mutated to alanines, the mAb 7G7 was not internalized (FIG. 6B) although this protein was clearly localized to the plasma membrane (FIG. 6A). This mutant did not co-distribute with internalized FITC-transferrin (FIGS. 6C and D). Internalization of mAb 7G7 was maintained in cells expressing the construct where the fourth leucine is mutated to alanine (Tac-MWNAL) (FIGS. 6F, G and H) whereas in cells expressing Tac-MWNLA, where the leucine at position 5 is mutated, the uptake of 7G7 was not detected (FIGS. 6J, K and L). Both these mutants were clearly expressed on the plasma membrane as revealed by non-permeablized staining using mAb 7G7 (FIGS. 6E and I). Taken together, these data demonstrate that the leucine at the fifth position is critical for PSMA internalization.

Figure 5:
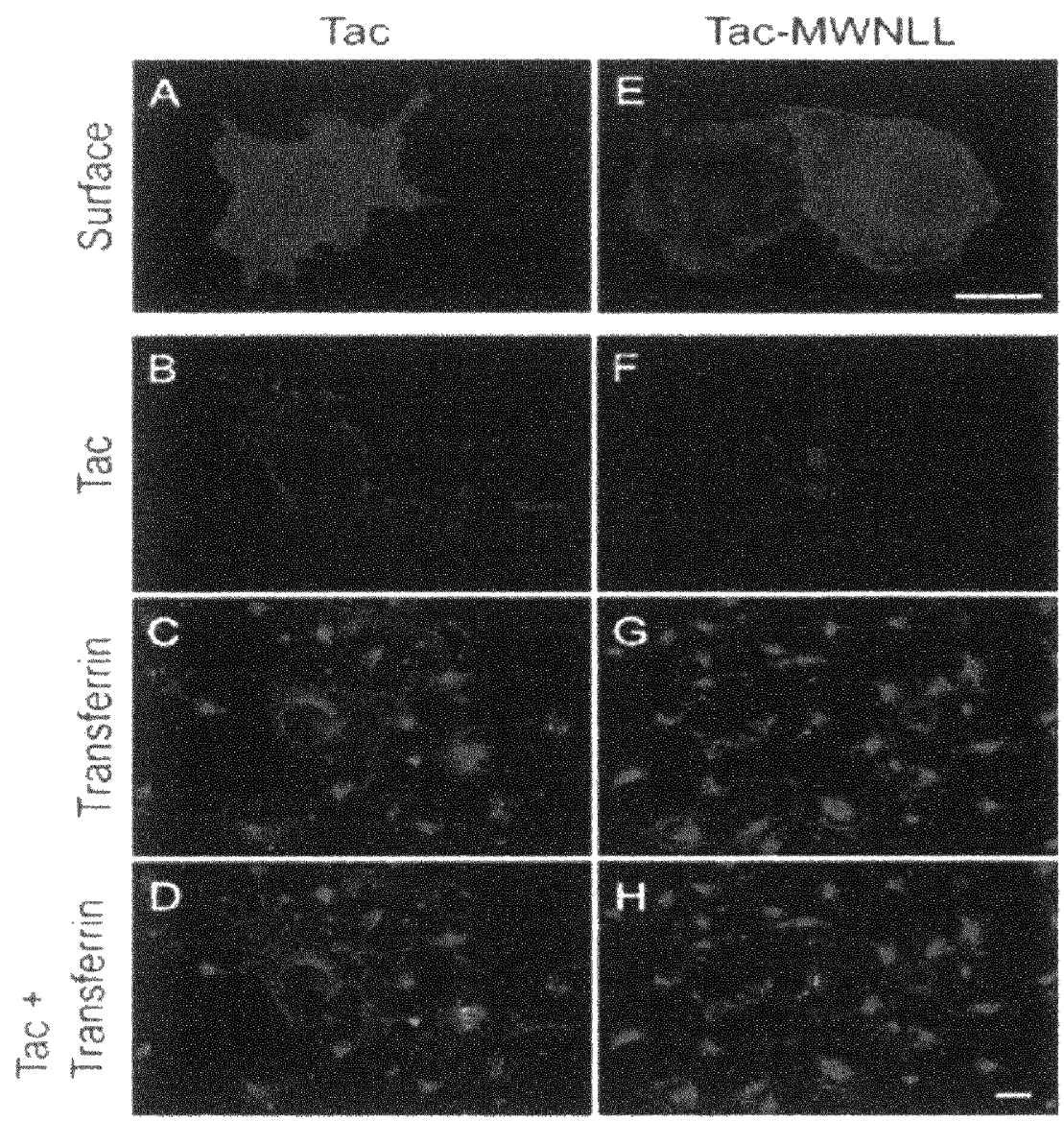
FIGS. 5A-5H provide confocal microscopy images showing internalization of Tac and Tac-PSMA chimera.
Figure 6:
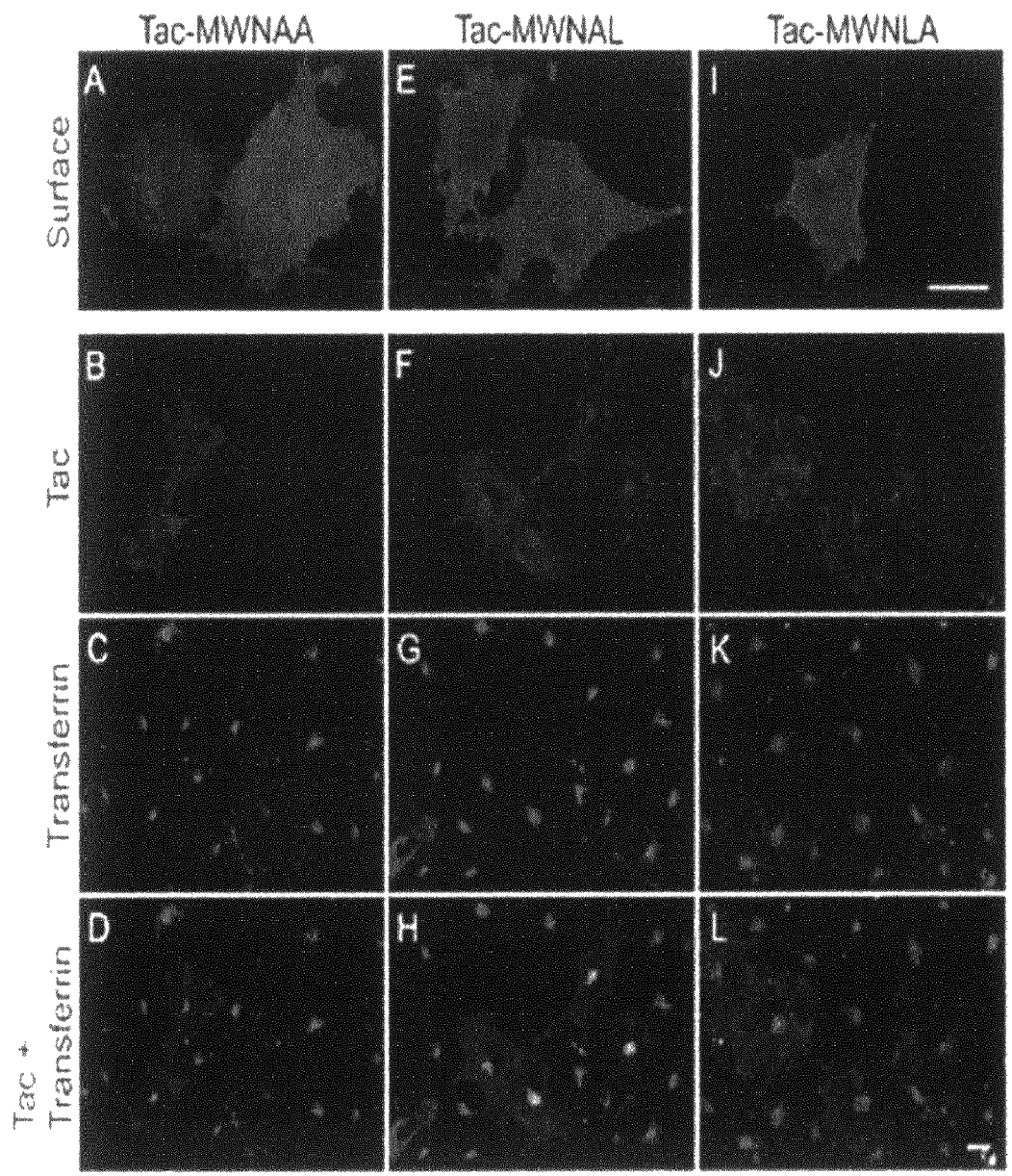
FIGS. 6A-6L provide confocal microscopy images showing internalization of Tac-PSMA chimeras harboring mutations in the di-leucine signal.

In FIG. 6, surface expression as well as internalization of PSMA was performed as described in for FIG. 5. FIGS. 6A, E and I show surface expression of Tac in COS-7 cells expressing Tac-MWNAA, Tac-MWNAL, and Tac-MWNLA chimeras, respectively. FIGS. 6B, F and J show the internalization of Tac chimera mutants. FIGS. 6C, G and K show the uptake of FITC-transferrin. FIGS. 6D, H and L are merged images. Representative medial optical sections are shown. A yellow color in H indicates the co-distribution of FITC-transferrin and internalized PSMA. In the figure, Bars=10µ (A, E and I) and 5µ (B, C, D, F, G, H, J, K, and L).

Figure 7:
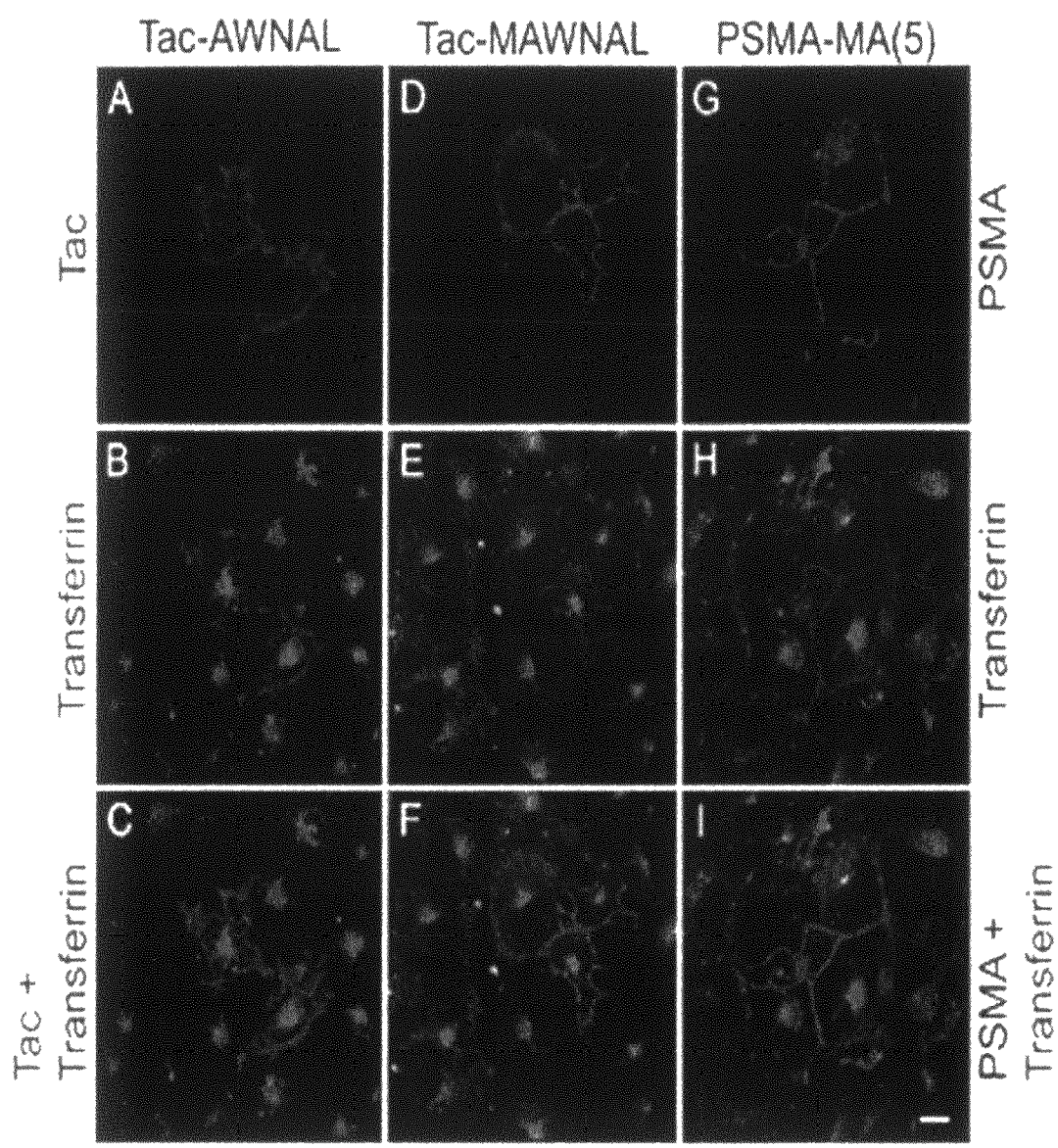
FIGS. 7A-7I provide confocal microscopy images showing internalization of Tac-PSMA chimeras Tac-AWNAL and Tac-MAWNAL, and of PSMA-MA (5)

While it is possible that a single leucine in the cytoplasmic tail of PSMA might play a crucial role in its internalization it is unlikely that it can function as an internalization motif. Therefore we decided to test for other potential amino acid residues in the five amino acid motif that might be involved in the internalization of PSMA. We have evidence that mutation of amino acids at position 2 and 3 and 4 (FIG. 3) of the cytoplasmic tail of PSMA did not affect internalization while mutation of leucine at position 5 abolished its internalization. The only amino acid that remained to be tested was the first amino acid methionine. Therefore, we mutated methionine in the internalizing Tac-MWNAL chimera to generate Tac-AWNAL. Although Tac-AWNAL was expressed on the cell surface, a drastic reduction in the internalization of mAb 7G7 was noticed in cells expressing this chimera (FIG. 7A). While in these cells FITC-transferrin was clearly internalized (FIG. 7B) there was little co-localization of internalized transferrin with Tac-AWNAL (FIG. 7C). Small amounts of internalized mAb J591 were seen in peripheral vesicles in contrast to the intense fluorescence of internalized transferrin seen at the cell center. This result indicated that in addition to the fifth leucine the methionine is also required and that the N-terminal five amino acids, MWNLL, form a motif to mediate the internalization of PSMA. To test whether the length of this motif is involved in PSMA internalization we inserted an additional alanine between tryptophan and methionine (Tac-MAWNAL) and monitored the internalization of this chimera. In COS cells, Tac-MAWNAL was clearly expressed on the cell surface as revealed by non-permeabilized staining. However, internalization of mAb7G7 was highly reduced (FIG. 7D) and there was less co-localization of the chimera with internalized FITC-transferrin (FIGS. 7E and F). We then tested whether incorporation of alanine into the MWNLL motif of PSMA itself affects internalization. Whereas insertion of one or two amino acids did not affect internalization, insertion of five alanines [PSMA-MA(5)] drastically reduced the internalization of PSMA (FIG. 7G).

FIGS. 7A and D show internalization of Tac chimera mutants and FIG. 7G shows mAb J591 in transiently transfected COS cells. FIGS. 7B, E and H show internalization of FITC-transferrin. FIGS. 7C, F and I are merged images. Note the lack of co-distribution of Tac-chimera mutants or PSMA-MA(5) and FITC-transferrin. In the figure, Bar=5µ.

Example 4

Adaptor Complex AP-2 is Involved with Internalization Mediated by the MXXXL Motif The endocytic motif of membrane receptors binds to adaptor protein complexes (AP), which are heterotetramers and mediate the internalization of membrane receptors. The adaptor complex AP-2 has been shown to associate with both tyrosine and di-leucine based signals. To obtain insights into whether AP-2 is involved in the internalization of PSMA we monitored internalization of PSMA in a HeLa cell line that expresses a dominant negative mutant µ2 of the AP-2 complex under the control of a tetracycline-off system. Strikingly, mutant µ2 drastically reduced the internalization of PSMA (FIG. 8A) and transferrin (FIG. 8B) and transferrin showed a more diffused localization pattern that co-distributed with PSMA (FIG. 8C). In non-induced cells that only express wild type µ2 PSMA as well as transferrin were clearly internalized (FIGS. 8D, E, and F) indicating that the µ2-subunit of AP-2 is involved in the internalization mediated by the MWNLL motif of PSMA.

Figure 8:
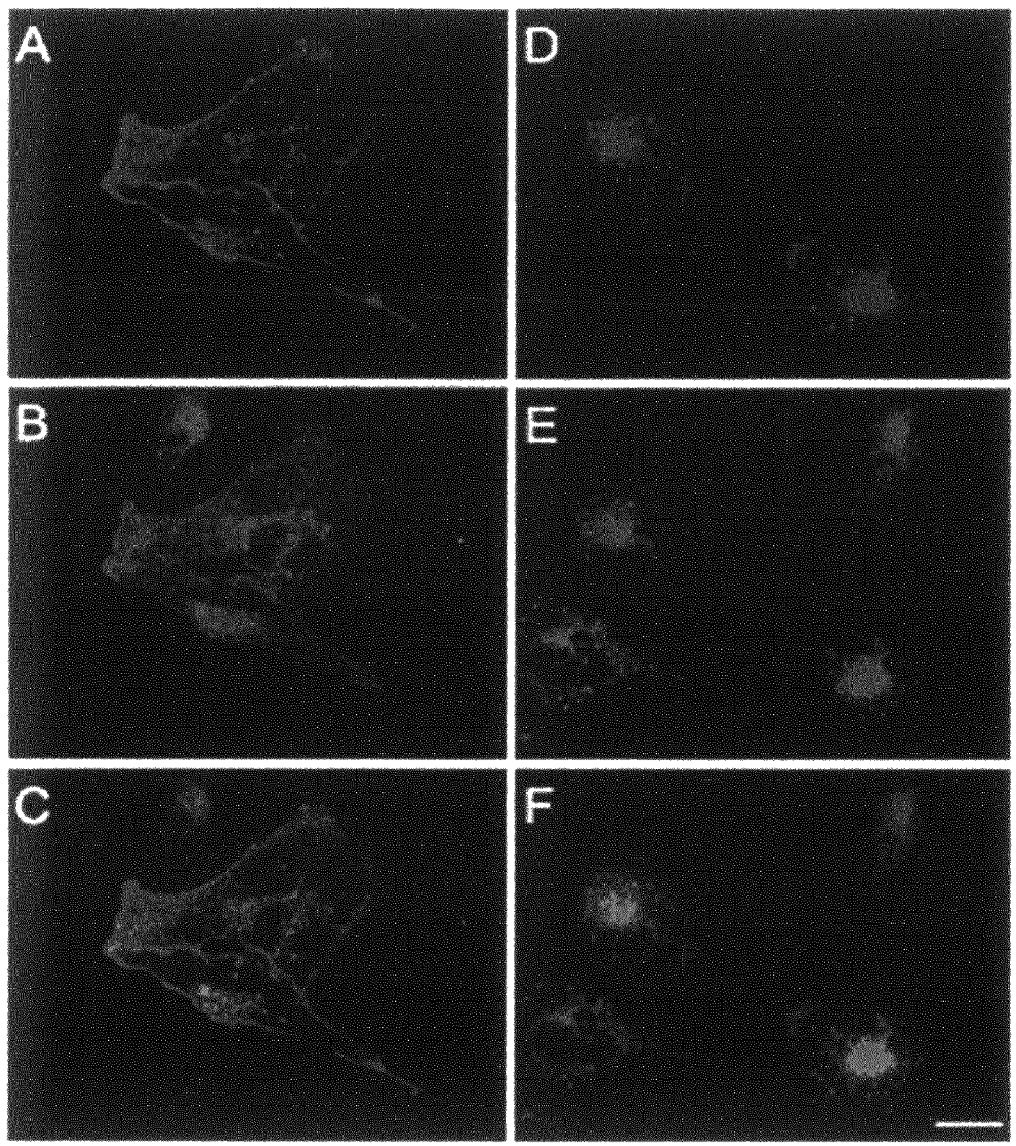
FIGS. 8A-8F provide confocal microscopy images showing internalization of $PSMA_{wt}$ in HeLa cells expressing dominant-negative AP-2 complexes.

In FIG. 8, $PSMA_{wt}$ cDNA was transiently transfected into HeLa cells expressing a tetracycline-repressible dominant-negative mutant of µ2. mAb J591 internalization was monitored in mutant µ2-induced cells (A) and in non-induced cells (D). FIGS. 8B and E show internalization of FITC-transferrin. FIGS. 8C and F are merged images. In the figure, Bar=5µ.

Discussion

In this study, we demonstrate that the cytoplasmic tail five N-terminal amino acids MWNLL are sufficient to mediate the internalization of PSMA. Methionine at the first position and leucine at the fifth position are essential whereas amino acids 2, 3, and 4 are dispensable for the internalization of PSMA. Incorporation of alanine/s into Tac-chimera (Tac-MAWNAL) and into PSMA [PSMA-MA(5)] drastically reduced the internalization indicating that the length of this sequence is also important for its internalization function. We also present evidence that the adaptor complex AP-2 is involved in the internalization of PSMA. Our results indicate that the N-terminal five amino acid residues of PSMA form a novel autonomous methionine-leucine based internalization motif (MXXXL). To our knowledge this is the first study describing a N-terminal amino acid (translation start site) as part of an internalization motif.

Although the presence of two consecutive leucines at position four and five suggested that the cytoplasmic tail of PSMA may contain a di-leucine like motif, our results indicate that this might not represent a typical di-leucine motif as observed in other membrane proteins. The di-leucine based signals of the [DE]XXXL[L1] and DXXLL types have an acidic residue at −4 from the first leucine which is absent in PSMA and is replaced by an essential methionine. In the [DE]XXXL[L1] type the first leucine is generally indispensable and substitution with other amino acids decreases the efficacy of the signal whereas in the DXXLL type both the leucines are essential and mutation of any of these residues to alanine inactivates the signal. In PSMA, mutation of the first leucine did not change significantly the internalization kinetics. Moreover, in polarized epithelial cells, proteins with di-leucine motif are targeted to the basolateral plasma membrane. By contrast, PSMA is targeted to the apical plasma membrane in MDCK cells and swapping the cytoplasmic tail of PSMA with the cytoplasmic tail of a di-leucine motif containing protein redirected PSMA to the basolateral plasma membrane. The absence of tyrosine residues in the cytoplasmic tail of PSMA clearly indicates that this protein does not contain a tyrosine-based signal. Taken together, these results strongly indicate that the MXXXL motif of PSMA is a novel methionine-leucine based internalization motif.

PSMA is localized to the recycling endosomal compartment as revealed by its co-localization with internalized transferring. Co-localization of Tac-MWNLL with transferrin further indicated that the MWNLL sequence is sufficient for the localization of PSMA to the recycling endosomal compartment. It appears that the cytoplasmic tail of PSMA associates with the actin cross linking protein filamin and that this association is involved in the localization of PSMA to the recycling endosomal compartment.

Figure 9:
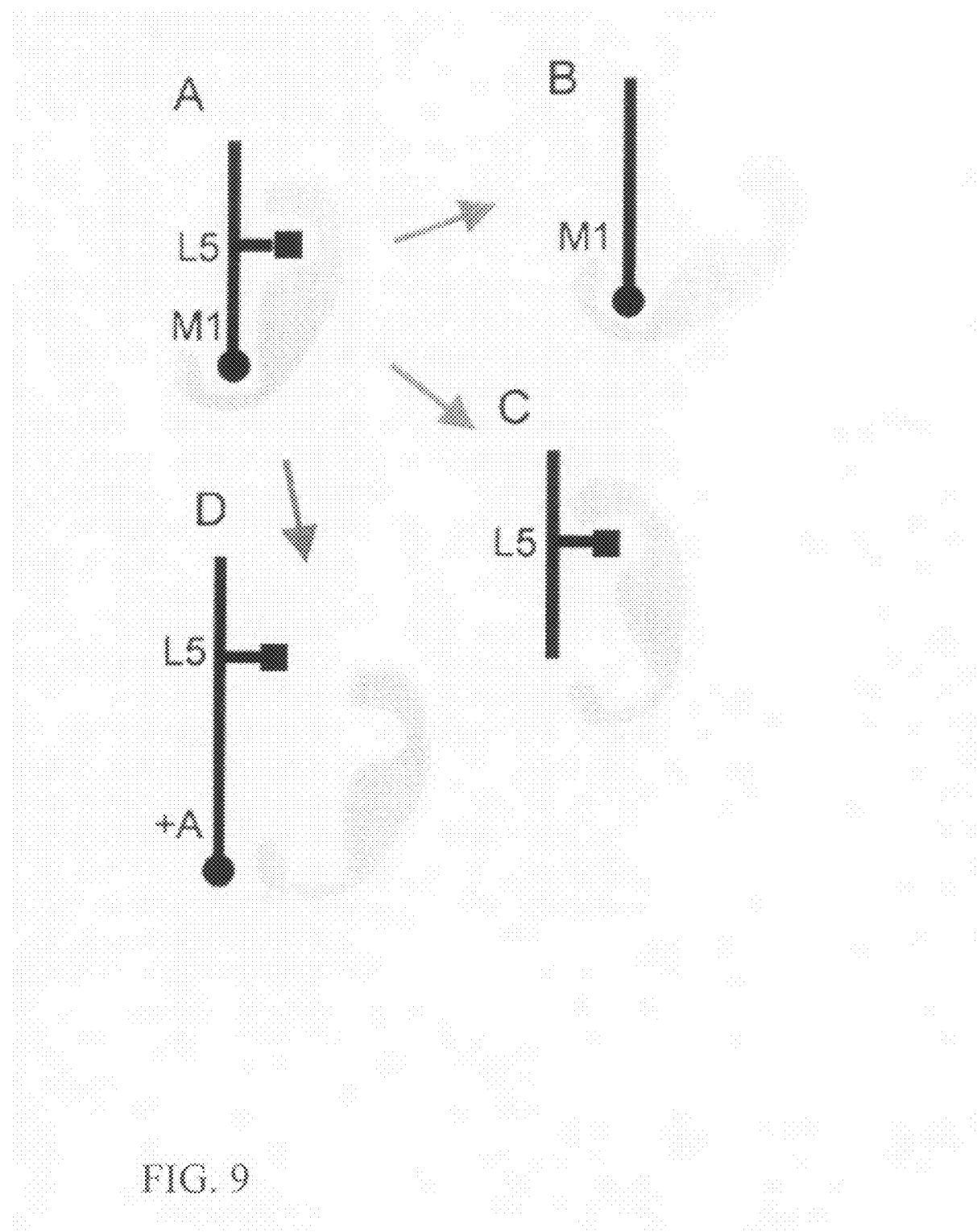
FIGS. 9A-9D are a schematic representation of a model of binding of the PSMA internalization motif to µ2 of the AP-2 complex.

We have shown that dominant negative µ2 of the AP-2 complex reduces the internalization of PSMA indicating that the AP-2 complex is involved in the internalization mediated by the MXXXL motif of PSMA. Recent structural studies suggested that the YxxΦ endocytic determinant might associate with the µ2 adaptin as a two pinned plug into a socket with the Y and the Φ residues (the pins) fitting into sterically and chemically complementary pockets of the µ2 surface. Requirement of the specific length of the MXXXL motif may indicate that the first amino acid methionine and the fifth leucine of the PSMA endocytic determinant might function as two pins fitting into a complementary pocket of µ2 (FIG. 9).

FIG. 9A shows that the endocytic determinant of PSMA might form two pins (methionine at position 1 (black circle) and leucine at position 5 (black square)) that fit into a complementary pocket of a µ2 (grey) associating with the cytoplasmic tail of PSMA. Loss of the side-chains of leucine-5 (FIG. 9B) or methionine-1 (FIG. 9C) of the internalization motif might result in an altered association of the adaptor preventing the internalization of PSMA. Similarly, extension of the length of the internalization motif with an additional alanine (FIG. 9D) might prevent the binding of the adaptor protein to the cytoplasmic tail of PSMA and therefore inhibit internalization of the protein.

The catalytic site for glutamate carboxypeptidase/NAALDAse activity of PSMA resides in its extracellular domain. Millimolar concentrations of phosphate used in the culture medium almost completely inhibited the NAALDase activity in COS cells. Since our internalization assays were performed in culture medium that inhibits NAALDase activity, this enzymatic activity appears not to be necessary for the internalization of PSMA. Moreover, in LNCaP cells, incubation with the NAAG substrate for NAALDase did not increase the internalization of PSMA whereas incubation with mAb J591 or the Fab fragments of this antibody increased the internalization rate of PSMA. The antibody and the antibody fragments might mimic a putative ligand for PSMA. These results indicate that the internalization of PSMA might be an independent function from its glutamate carboxipeptidase/NAALDase activity.

Example 5

Delivery of a cytotoxic agent to bladder cancer cells or prostate cancer cells, in culture or a subject's body, is described in this prospective example. A chimeric transmembrane protein can be prepared by adding the MXXXL internalization motif to the non-internalized protein Tac, as described in Example 3. An expression vector encoding the MXXXL-Tac chimeric protein under the control of the uroplakin II promoter, for specific expression in bladder cells, or under the control of the probasin promoter, for specific expression in prostate cells, can be administered to the cells as a DNA/liposome complex. Following expression of the chimeric membrane protein on the cell surface, monoclonal antibody mAb 7G7 conjugated to a cytotoxic agent can be administered to the cells.

In this prospective example, mAB 7G7 can be conjugated to the maytansinoid antitumor agent DM1, which is a potent inhibitor of microtubule formation and a disruptor of mitosis. Purified mAB 7G7 can be modified with N-succinimidyl-4-(2-pyridylthio)pentanoate (SPP) to introduce dithiopyridyl groups. The antibody (e.g., at about 6-10 mg/mL) in potassium phosphate buffer (PPB; e.g., 50 mM PPB at pH 6.5) containing NaCl (50 mM) and EDTA (1 mM) can be treated with SPP (e.g. at 5.3 molar equivalents in 2.3 mL ethanol). After incubation for 90 minutes under argon at ambient temperature, the reaction mixture can be filtered following standard procedures e.g., by gel filtration through a Sephadex G25 column equilibrated with 35 mM sodium citrate, 154 mM NaCl, 2 mM EDTA. Antibody containing fractions can be pooled and assayed. The modified antibody (e.g., with 9.5 .mu.mols of releasable 2-thiopyridine groups) can be diluted with the above 35 mM sodium citrate buffer, pH 6.5, to a final concentration of e.g., 2.5 mg/mL. DM1 (e.g., at 1.7 equivalents, 16.1 .mu.mols) in 3.0 mM dimethylacetamide (DMA, 3% v/v in the final reaction mixture) can then be added to the antibody solution. The reaction can proceed at ambient temperature under argon for 20 hours. The reaction can be loaded on a gel filtration column, e.g., Sephacryl S300 gel filtration column (5.0 cm.times.90.0 cm, 1.77 L) equilibrated with 35 mM sodium citrate, 154 mM NaCl, pH 6.5. The flow rate can be at e.g., 5.0 mL/min, and 65 fractions (20.0 mL each) can be collected. The major peak comprising mAB 7G-DM1 can be collected and the number of DM1 drug molecules linked per antibody molecule determined, e.g., by measuring the absorbance at 252 nm and 280 nm.

The mAB 7G7-DM1 conjugate administered to the MXXXL-Tac expressing cells can be internalized following binding to the chimeric MXXXL-Tac protein. Internalized DM1 can display its cytotoxic activity in the cells.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, manufacture, composition of matter, means, methods and/or steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, manufacture, compositions of matter, means, methods, or steps.

The invention claimed is:

1. A chimeric transmembrane protein comprising:
   a membrane-spanning polypeptide; and
   an internalization motif, having the sequence $MX_1X_2X_3L$, wherein $MX_1X_2X_3L$ is selected from the group consisting of SEQ ID NO: 24, SEQ ID NO: 25; SEQ ID NO: 26, and SEQ ID NO: 27; $LX_3X_2X_1M$ wherein $LX_3X_2X_1M$ is selected from the group consisting of SEQ ID NO: 28, SEQ ID NO: 29, SEQ ID NO: 30, and SEQ ID NO: 31, connected to the membrane-spanning polypeptide;
   wherein at least a portion of the membrane-spanning polypeptide is heterologous to the internalization motif,
   the internalization motif occurs at a cytoplasmically located part of the chimeric transmembrane protein, and
   wherein the chimeric transmembrane protein is internalized when expressed in the plasma membrane of a eukaryotic cell.

2. The chimeric transmembrane protein of claim 1, wherein the amino acid sequence of the membrane-spanning polypeptide is obtained or derived from an integral membrane protein.

3. The chimeric transmembrane protein of claim 2, wherein the integral membrane protein is not capable of being internalized.

4. The chimeric transmembrane protein of claim 1, wherein the membrane-spanning polypeptide is entirely heterologous to the internalization motif.

5. The chimeric transmembrane protein of claim 1, wherein the membrane-spanning polypeptide comprises amino acid sequences derived from two or more proteins.

6. The chimeric transmembrane protein of claim 1, wherein the heterologous portion of the membrane-spanning polypeptide comprises an amino acid sequence obtained or derived from an integral membrane protein.

7. The chimeric transmembrane protein of claim 6, wherein the integral membrane protein is a non-internalized integral membrane protein.

8. The chimeric transmembrane protein of claim 1, wherein the heterologous portion of the membrane-spanning polypeptide contains at least one transmembrane region.

9. The chimeric transmembrane protein of claim 1, wherein the heterologous portion of the membrane-spanning polypeptide lacks a transmembrane region.

10. The chimeric transmembrane protein of claim 1, wherein the heterologous portion of the membrane-spanning polypeptide provides part of a transmembrane region.

11. The chimeric transmembrane protein of claim 1, wherein the internalization motif is located at the N- or C-terminus of the chimeric transmembrane protein, forming a cytoplasmic tail.

12. The chimeric transmembrane protein of claim 11, wherein the internalization motif at the N-terminus of the chimeric transmembrane protein is of the sequence $MX_1X_2X_3L$, wherein $MX_1X_2X_3L$ is selected from the group consisting of SEQ ID NO: 24, SEQ ID NO: 25; SEQ ID NO:

26, and SEQ ID NO: 27; and the internalization motif at the C-terminus of the chimeric transmembrane protein is of the sequence $LX_3X_2X_1M$, wherein $LX_3X_2X_1M$ is selected from the group consisting of SEQ ID NO: 28, SEQ ID NO: 29, SEQ ID NO: 30, and SEQ ID NO: 31.

13. A chimeric transmembrane protein comprising:
a membrane-spanning polypeptide; and
an internalization motif, of the sequence $MX_1X_2X_3L$, wherein $MX_1X_2X_3L$ is selected from the group consisting of SEQ ID NO: 24, SEQ ID NO: 25; SEQ ID NO: 26, and SEQ ID NO: 27; or $LX_3X_2X_1M$, wherein $LX_3X_2X_1M$ is selected from the group consisting of SEQ ID NO: 28, SEQ ID NO: 29, SEQ ID NO: 30, and SEQ ID NO: 31, connected to the membrane-spanning polypeptide;

wherein at least a portion of the membrane-spanning polypeptide is heterologous to the internalization motif,
the internalization motif is located at the N- or C-terminus of the chimeric transmembrane protein, forming a cytoplasmic tail, and
the chimeric transmembrane protein is internalized when expressed in the plasma membrane of a eukaryotic cell;
wherein the membrane-spanning polypeptide has an amino acid sequence obtained or derived from the α-chain of the interleukin-2 receptor, and the internalization motif has the sequence $LX_3X_2X_1M$ which is located at the C-terminus of the chimeric transmembrane protein.

* * * * *